United States Patent [19]

Han et al.

[11] Patent Number: 5,068,486

[45] Date of Patent: Nov. 26, 1991

[54] PROCESS FOR DIRECT OXIDATIVE CONVERSION OF METHANE TO HIGHER HYDROCARBONS AT HIGH PRESSURE AND MODERATE TEMPERATURE

[75] Inventors: Scott Han, Lawrenceville; Daniel J. Martenak, Trenton; Robert E. Palermo, Bloomfield, all of N.J.; Dennis E. Walsh, Richboro, Pa.

[73] Assignee: Mobil Oil Corp., Fairfax, Va.

[21] Appl. No.: 597,221

[22] Filed: Oct. 15, 1990

[51] Int. Cl.$^5$ .............................................. C07C 2/00
[52] U.S. Cl. .................................... 585/500; 585/700; 585/943; 585/652; 423/415 A
[58] Field of Search ............... 585/500, 700, 943, 652; 423/415 A

[56] References Cited

U.S. PATENT DOCUMENTS

| | | | |
|---|---|---|---|
| 1,995,136 | 3/1935 | Winkler et al. | 585/500 |
| 4,554,395 | 11/1985 | Jones et al. | 585/500 |
| 4,634,800 | 1/1987 | Withers, Jr. et al. | 585/700 |
| 4,929,787 | 5/1990 | Cameron et al. | 585/943 |
| 4,935,572 | 6/1990 | Erekson et al. | 585/700 |
| 4,962,261 | 10/1990 | Abrevaya et al. | 585/943 |

FOREIGN PATENT DOCUMENTS 2603577 9/1986 France ..................... 585/700

*Primary Examiner*—Anthony McFarlane
*Assistant Examiner*—Nhat Phan
*Attorney, Agent, or Firm*—Alexander J. McKillop; Charles J. Speciale; Edward F. Kenehan, Jr.

[57] ABSTRACT

There is provided a process for converting methane to hydrocarbons having at least two carbon atoms. The process involves contacting methane with an oxidizing agent, such as oxygen, at a relatively moderate temperature of less than about 700° C. and a relatively high pressure of greater than about 20 atmospheres.

8 Claims, No Drawings

PROCESS FOR DIRECT OXIDATIVE CONVERSION OF METHANE TO HIGHER HYDROCARBONS AT HIGH PRESSURE AND MODERATE TEMPERATURE

BACKGROUND

There is provided herein a process for converting methane to hydrocarbons having at least two carbon atoms (i.e. $C_2+$ hydrocarbons). The processes involves contacting methane with an oxidizing agent, such as oxygen, under conditions of high pressure and moderate temperature.

Natural gas is an abundant fossil fuel resource. Recent estimates places worldwide natural gas reserves at about $35 \times 10^{14}$ standard cubic feet, corresponding to the energy equivalent of about 637 billion barrels of oil.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85-95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficulty accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for other ways to convert natural gas to higher valued and/or more readily transportable products.

Oxidative coupling is a process for the direct conversion of methane to higher hydrocarbons. It is normally performed at 700°-900° C. and less than 10 atm. While successful lower temperature operation has been a sought after goal, it has been found that at temperatures below about 700° C., the selectivity to $C_2+$ products rapidly diminishes, and below about 650° C. $C_2+$ production is essentially nil.

A second type of direct upgrading process is partial oxidation of methane to useful oxygenate products (i.e. methanol or formaldehyde). This approach operates at much higher pressures (20-100 atm.), but at more moderate temperatures (350°-450° C.) than oxidative coupling.

SUMMARY

There is provided herein a process for converting methane to hydrocarbons having at least two carbon atoms, said process comprising contacting said methane with an oxidizing agent under conditions sufficient to produce said hydrocarbons, said conditions including a temperature of from about 500° to about 700° C. and a pressure of from about 20 to about 100 atmospheres.

EMBODIMENTS

In the instant invention it has been discovered that, by processing in what is believed to be a hitherto unexplored operating regime, $C_2+$ products can be preferentially obtained at temperatures well below those characteristic of oxidative coupling. The operating regime of the instant invention encompasses elevated pressures (e.g., about 20-150 atm.), which are atypical of oxidative coupling, and temperatures intermediate between those of direct partial oxidation and oxidative coupling (about 500°-700° C.).

The feed for the instant process could be either pure methane or methane as the major component of natural gas. Oxygen or air are the preferred oxidizers, though other oxidizers such as nitrous oxide, ozone, hydrogen peroxide, sulfur, etc. may be used. Also, yields may be further improved by the use of certain catalysts, especially known oxidative coupling catalysts as described in the extensive literature on the subject. Examples of such oxidative coupling catalysts include non-reducible oxides, transition metal oxides, rare earth oxides and oxides of the elements of Groups IIIB, IVB and VB of the Periodic Table. Particular examples of such oxides include oxides of Mg, Ba, Ca, Mn, Ni, Sm and Pb. The oxides may optionally be modified, e.g., with alkali metal salts such as LiCl.

The present reaction conditions may include a temperature of from about 500° C. to about 700° C., e.g., from about 525° C. to about 625° C., and a pressure of from about 20 atm to about 150 atm, e.g., from about 40 atm to about 80 atm. In addition to the above described operating conditions, other preferred operating parameters include residence times from about 0.01 to 120 sec., and, more particularly, from about 0.1 to 10 sec., and an oxidizer mole fraction in the feed from about 5-50%.

The present reaction conditions may include a gas hourly space velocity of from about 1000 hr$^{-1}$ to about 500,000 hr$^{-1}$.

Residence time is defined a the product of the isothermal reactor volume multiplied by its void fraction, that product being divided by the total NTP volumetric feed rate corrected to reactor temperature and pressure. For an empty reactor the void fraction is 1.0, while, for an packed reactor, it can range typically from ~0.3 to ~0.6. In non-catalytic operation, the reactor may be packed with an inert material such as sand or vycor. In catalytic operation, catalyst accounts for at least a portion of the total packed volume. It will be understood that NTP refers to room temperature (i.e. about 25° C.) and atmospheric pressure.

Total feed flow rate and feed oxygen content are choosen not only in accordance with attaining the desired residence time, but also to conform to the available heat removal capability. This insures that available heat transfer capacity is adequate to accommodate the heat release rates per unit reactor volume and thus to maintain the reactor temperature within acceptable bounds at the desired conversion levels.

EXAMPLE

Methane was contacted with oxygen under the conditions set forth in Table 1. The results of these reactions are also summarized in Table 1.

TABLE 1

| | | |
|---|---|---|
| Temperature, C. | 550 | 550 |
| Pressure, psig | 50 | 900 |
| Residence Time (sec.) | 0.6 | 0.6 |
| Mole % oxygen in feed | 14 | 15 |
| Methane Conv., % | ~0.5 | 12.6 |
| Oxygen Consumption, % | 3.4 | 100 |
| Product Selectivities | | |
| Carbon Monoxide | 0 | 57 |
| Carbon Dioxide | 100 | 10 |
| Methanol | 0 | 1 |
| C2+ | 0 | 32* |

*16% ethane, 12% ethylene, 3% acetylene, 1% propane

The effectiveness of process in the present regime is shown by the data in Table 1. As discussed above, operating at pressures characteristic of oxidative coupling but at a temperature well below that typical of such processing resulted in incomplete oxygen consumption (and therefore low methane conversion), high C0$_2$ selectivity, and the expected absence of C$_2$+ products. Increasing pressure to about 60 atm at otherwise identical conditions resulted in complete oxygen consumption, about 13% methane conversion, and about 32% C2+ selectivity. Note also that methanol production, which would be expected at these pressures, but at the lower temperatures typical of direct partial oxidation is very low. Thus, the results obtained at the conditions of this invention are quite unexpected.

What is claimed is:

1. A process which takes place in the absence of a catalyst for converting methane to hydrocarbons having at least two carbon atoms, said process comprising contacting said methane with an oxidizing agent in the absence of a catalyst under conditions sufficient to produce said hydrocarbons, said conditions including a temperature of from about 500° to about 700° C. and a pressure of from about 20 to about 150 atmospheres.

2. A process according to claim 1, wherein natural gas is contacted with said oxidizing agent.

3. A process according to claim 1, wherein said oxidizing agent is oxygen.

4. A process according to claim 1, wherein said oxidizing agent is air.

5. A process according to claim 1, wherein said conditions further include a gas hourly space velocity of from about 1000 hr$^{-1}$ to about 500,000 hr$^{-1}$.

6. A process according to claim 5, wherein the oxidizer mole fraction in the feed is from about 5 to about 50%.

7. A process according to claim 1, wherein said conditions include a temperature of from about 525° C. to about 625° C.

8. A process according to claim 7, wherein said conditions include a pressure of from about 40 atm to about 80 atm.

* * * * *